United States Patent
Sharonov

(10) Patent No.: US 9,585,600 B2
(45) Date of Patent: Mar. 7, 2017

(54) MAGNETIC FIELD VIEWING FILM FOR TRACKING IN-SITU SURGICAL APPLICATIONS

(71) Applicant: Covidien LP, Mansfield, MA (US)

(72) Inventor: Alexey Sharonov, Bethany, CT (US)

(73) Assignee: Covidien LP, Mansfield, MA (US)

( * ) Notice: Subject to any disclaimer, the term of this patent is extended or adjusted under 35 U.S.C. 154(b) by 398 days.

(21) Appl. No.: 13/948,420

(22) Filed: Jul. 23, 2013

(65) Prior Publication Data

US 2014/0094685 A1   Apr. 3, 2014

Related U.S. Application Data

(60) Provisional application No. 61/708,670, filed on Oct. 2, 2012.

(51) Int. Cl.
- *A61B 6/00* (2006.01)
- *A61B 5/06* (2006.01)
- *A61F 2/00* (2006.01)
- *A61F 2/82* (2013.01)

(52) U.S. Cl.
CPC ............... *A61B 5/065* (2013.01); *A61B 5/062* (2013.01); *A61F 2/0063* (2013.01); *A61F 2/82* (2013.01); *A61B 2034/2051* (2016.02); *A61B 2034/2065* (2016.02); *A61B 2505/05* (2013.01); *A61F 2210/009* (2013.01); *A61F 2250/0096* (2013.01)

(58) Field of Classification Search
CPC ................................ A61B 5/062; A61B 5/065
USPC .................................................. 600/409, 424
See application file for complete search history.

(56) References Cited

U.S. PATENT DOCUMENTS

| | | |
|---|---|---|
| 4,489,711 A | 12/1984 | Latzke |
| 5,342,608 A | 8/1994 | Moriya et al. |
| 5,944,023 A * | 8/1999 | Johnson et al. ............... 600/424 |
| 6,344,021 B1 | 2/2002 | Juster et al. |
| 6,941,165 B2 | 9/2005 | Nakai et al. |
| 7,176,344 B2 | 2/2007 | Gustafson et al. |
| 7,301,332 B2 | 11/2007 | Govari et al. |
| 7,409,953 B2 | 8/2008 | Griesbach, III |
| 7,494,686 B2 | 2/2009 | Suh et al. |
| 7,702,378 B2 | 4/2010 | Bolan et al. |
| 2004/0138552 A1 | 7/2004 | Harel et al. |
| 2005/0242805 A1 | 11/2005 | Honkura et al. |

(Continued)

FOREIGN PATENT DOCUMENTS

| | | |
|---|---|---|
| EP | 1107043 A2 | 6/2001 |
| JP | 2004074486 A | 3/2004 |

OTHER PUBLICATIONS

An extended European Search Report issued in Applicaiton No. 13186828.3 dated Dec. 2, 2013.

(Continued)

*Primary Examiner* — James Kish
*Assistant Examiner* — Michael N Fisher

(57) ABSTRACT

A method is provided. The method includes placing a magnetic field viewing film over a region of tissue; inserting at least one of a medical device or a medical instrument comprising at least one magnetic element into the region of the tissue; and determining a location of at least one of the medical device or the medical instrument based on a visualization by the magnetic field viewing film of a magnetic field produced by the at least one magnetic element.

13 Claims, 7 Drawing Sheets

(56) References Cited

U.S. PATENT DOCUMENTS

| | | |
|---|---|---|
| 2007/0293878 A1 | 12/2007 | Butsch |
| 2010/0087731 A1* | 4/2010 | Ramachandran ............. 600/424 |
| 2010/0114126 A1* | 5/2010 | Neff ...................... A61B 17/52 |
| | | 606/151 |
| 2010/0121323 A1* | 5/2010 | Pool et al. ...................... 606/54 |
| 2010/0168612 A1* | 7/2010 | Ducharme et al. ........... 600/567 |
| 2011/0184440 A1 | 7/2011 | Saldinger |

OTHER PUBLICATIONS

Chinese Office Action issued in Appl. No. CN 2013104609550 dated Aug. 29, 2016.

\* cited by examiner

MAGNETIC FIELD VIEWING FILM FOR TRACKING IN-SITU SURGICAL APPLICATIONS

CROSS-REFERENCE TO RELATED APPLICATIONS

This application claims the benefit of and priority to U.S. Provisional Patent Application No. 61/708,670, filed Oct. 2, 2012, the entire disclosure of which is incorporated by reference herein.

BACKGROUND

Technical Field

The present disclosure relates to systems, apparatuses and methods for tracking medical devices. More particularly, the present disclosure relates to systems, apparatuses and methods for tracking invasive medical devices using magnetic field sensitive viewing films.

Background of Related Art

During invasive surgery it is often desired to track location of medical devices (e.g., surgical instruments, implants, sponges, etc.) and internal features (e.g., tissue, organs, blood vessels, etc.) within the patient. Conventional tracking usually involves magnetic resonance or X-ray fluoroscopy systems. These systems rely on sophisticated and expensive equipment such as computers and displays for visualizing location of the medical devices. Further, in the case of X-ray fluoroscopy the patient and the attending medical staff are exposed to undesirable X-ray radiation.

There is continual need for medical device tracking systems, apparatuses and methods that provide for safe, accurate, real-time tracking of medical devices that do not require additional computing and visualization equipment.

SUMMARY

The present disclosure provides for a method including: placing a magnetic field viewing film over a region of tissue; inserting at least one of a medical device or a medical instrument including at least one magnetic element into the region of the tissue; and determining a location of at least one of the medical device or the medical instrument based on a visualization by the magnetic field viewing film of a magnetic field produced by the at least one magnetic element.

According to one aspect of the present disclosure, the medical device is selected from the group consisting of a mesh, a stent, a sponge, a fastener, a sling, a suture, a clip, and combinations thereof.

According to one aspect of the present disclosure, the medical instrument is selected from the group consisting of an endoscope, a catheter, a grasper, a balloon, a sealer, a tissue stapler, a vessel sealer, a clip applier, a biopsy instrument, an ablation probe, and combinations thereof.

According to one aspect of the present disclosure, the medical device is at least one of a hernia mesh or a stent including a plurality of magnetic microparticles disposed thereon in a predetermined pattern.

According to one aspect of the present disclosure, the magnetic field viewing film includes at least one flexible sheet and a plurality of magnetic particles responsive to the magnetic field produced by the at least one magnetic element.

According to one aspect of the present disclosure, the method further includes adjusting the location of at least one of the medical device or the medical instrument based on the visualization by the magnetic field viewing film of the magnetic field produced by the at least one magnetic element.

The present disclosure provides for a method including: placing a magnetic field viewing film over a region of tissue; guiding a medical device using a medical instrument into the region of the tissue, wherein at least one of the medical device or the medical instrument comprises at least one magnetic element; and determining location of at least one of the medical device or the medical instrument based on a visualization by the magnetic field viewing film of a magnetic field produced by the at least one magnetic element.

According to one aspect of the present disclosure, features relevant to targeting the procedure, tissue or the medical device may be sketched on the magnetic field viewing film using a magnetized stylus or "pen".

According to one aspect of the present disclosure, the medical device is selected from the group consisting of a mesh, a stent, a sponge, a fastener, a sling, a suture, a clip, and combinations thereof.

According to one aspect of the present disclosure, the medical instrument is selected from the group consisting of a endoscope, a catheter, a grasper, a balloon, a sealer, a tissue stapler, a vessel sealer, a clip applier, a biopsy instrument, an ablation probe, and combinations thereof.

According to one aspect of the present disclosure, the medical device is selected from the group consisting of a hernia mesh and a stent including a plurality of magnetic microparticles disposed thereon in a predetermined pattern.

According to one aspect of the present disclosure, the method further includes adjusting the location of the medical device based on the visualization by the magnetic field viewing film of the magnetic field produced by the at least one magnetic element.

According to one aspect of the present disclosure, the magnetic field viewing film includes at least one flexible sheet and a plurality of microspheres encapsulating at least one magnetic particle responsive to the magnetic field produced by the at least one magnetic element.

The present disclosure provides for a kit including: a magnetic field viewing film; and at least one of a medical instrument or a medical device, wherein at least one of the medical instrument or the medical device includes at least one magnetic element configured to produce a magnetic field that is visualized by the magnetic field viewing film.

According to one aspect of the present disclosure, the kit further includes instructions for use of the kit, the instructions including: placing the magnetic field viewing film over a region of tissue; inserting at least one the medical device or the medical instrument into the region of the tissue; and determining location of at least one of the medical device or the medical instrument based on a visualization by the magnetic field viewing film of the magnetic field produced by the at least one magnetic element.

According to one aspect of the present disclosure, the instructions further include adjusting the location of at least one of the medical device or the medical instrument based on the visualization of the magnetic field viewing film.

According to one aspect of the present disclosure, the medical device is selected from the group consisting of a mesh, a stent, a sponge, a fastener, a sling, a suture, a clip, and combinations thereof.

According to one aspect of the present disclosure, the medical instrument is selected from the group consisting of an endoscope, a catheter, a grasper, a balloon, a sealer, a tissue stapler, a vessel sealer, a clip applier, a biopsy instrument, an ablation probe, and combinations thereof.

According to one aspect of the present disclosure, the medical device is a hernia mesh including a plurality of magnetic microparticles disposed thereon in a predetermined pattern.

According to one aspect of the present disclosure, the medical device is a stent including a plurality of magnetic microparticles disposed thereon in a predetermined pattern.

According to one aspect of the present disclosure, the magnetic field viewing film includes at least one flexible sheet and a plurality of magnetic particles responsive to the magnetic field produced by the at least one magnetic element.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure provides for a system and method for visualization of location of internal tissue features and/or medical devices. The system includes a magnetic field visualization film disposed on an exterior portion of the patient (e.g., outside the abdominal cavity). The film is configured to change visually (e.g., darken) when brought in proximity of a magnetic field. Medical devices that are to be visualized are magnetized and/or include magnetic elements disposed thereon such that the magnetic field is visualized by the film. Visualization of internal tissues may be accomplished by locating one or more magnetic elements in proximity and/or contact with the internal tissues that are desired to be visualized. Changes in the color density of the film allow the user to locate and/or track location of the medical device.

Figure 1:
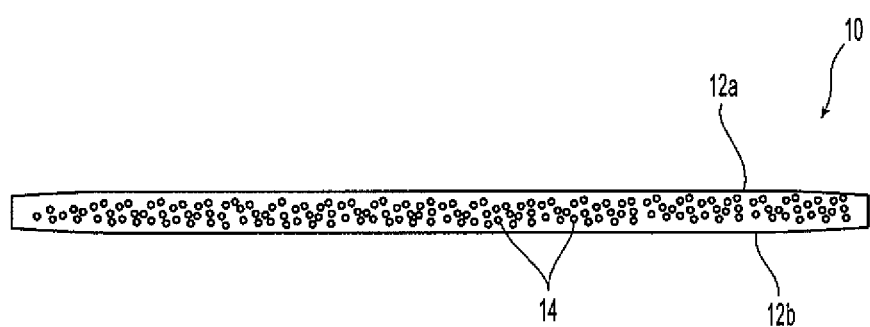
FIG. 1 is a side, cross-sectional view of a magnetic field visualization film according to the present disclosure.

With reference to FIG. 1, a magnetic field visualization film 10 is shown. The film 10 includes a top sheet 12a and a bottom sheet 12b, which may be formed from any non-magnetic, flexible, transparent or translucent material that allows for transmission of magnetic fields and light to pass therethrough. Suitable materials for forming the sheets 12a, 12b include thermoplastics, such as acrylics, celluloid, cellulose acetate, cyclic olefin copolymer, ethylene-vinyl acetate, fluoropolymers, ionomers, polyoxymethylene, polyacrylates, polyacrylonitrile, polyamide, polyamide-imide, polyaryletherketon, polybutadiene, polybutylene, polybutylene terephthalate, polycaprolactone, polychlorotrifluoroethylene, polyethylene terephthalate, polycyclohexylene dimethylene terephthalate, polycarbonate, polyhydroxyalkanoates, polyketones, polyester, polyethylene, polyetheretherketone, polyetherketoneketone, polyetherimide, polyethersulfone, chlorinated polyethylene, polyimide, polylactic acid, polymethylpentene, polyphenylene oxide, polyphenylene sulfide, polyphthalamide, polypropylene, polystyrene, polysulfone, polytrimethylene terephthalate, polyurethane, polyvinyl acetate, polyvinyl chloride, polyvinylidene chloride, styrene-acrylonitrile, and combinations thereof. One type of such magnetic field visualization film is commercially available under the trade name Magne-View from Magne-Rite, Inc.

Figure 2:
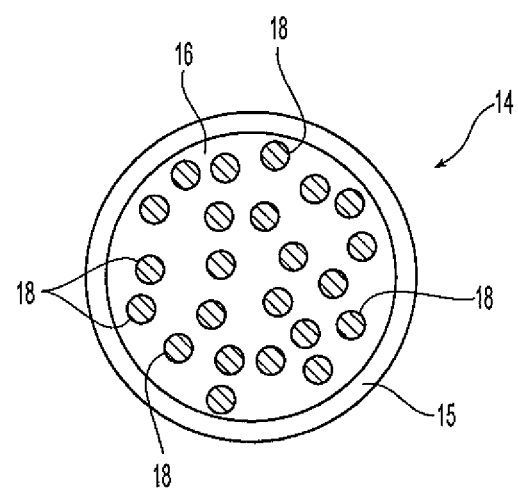
FIG. 2 is a side, cross-sectional view of a magnetic microsphere of the magnetic field visualization film of FIG. 1 according to the present disclosure.

The film 10 includes a plurality of microspheres 14 disposed between the sheets 12a, 12b. FIG. 2 shows an enlarged, cross-sectional view of the microsphere 14 including a membrane 15 enclosing a viscous fluid 16 and a plurality of magnetic particles 18 dispersed and suspended therein. The microspheres 14 may be formed by any suitable microencapsulation methods, such as emulsion-based solvent evaporation and/or extraction methods including, but not limited to, single-emulsion methods such as oil-in-water (o/w) and water-in-oil (w/o), double-emulsion methods such as water-in-oil-in-water (w/o/w) and solid-in-oil-in-water (s/o/w), and non-emulsion based methods, such as fluidized-bed, spray-drying, and casting/grinding methods. After encapsulations, the microspheres 14 may be deposited on the sheets 12a, 12b and cross-linked.

The fluid 16 may be an oil having an absolute viscosity at room temperature from about 50 centipoise (P) to 1,000 about cP, in embodiments from about 100 cp to about 500 cp. Suitable oils include, but are not limited to, petroleum-based oils, such as light, medium or heavy mineral oils (e.g., mixtures of alkanes having from about 40 carbons to about 60 carbons), plant-based oils, such as cottonseed oil, silicone-based oils, and combinations thereof. The fluid 15 may be used as a continuous phase fluid during the emulsification processes.

The magnetic particles 18 may be from about 10 angstroms (Å) to about 1000 Å, in embodiments from about 25 Å to about 500 Å. The magnetic or magnetized particles 18 formed from any suitable ferromagnetic or magnetizable material including, but not limited to, ferrite, strontium ferrous oxide, neodymium (NdFeB, optionally including dysprosium), samarium, cobalt, aluminum, nickel, copper, iron, titanium, and combinations thereof. In embodiments, magnetic particles 18 may have any suitable shape, such as, cylindrical, polygonal, (e.g., square or hexagonal cross-section), and the like. In further embodiments, the magnetic particles 18 may be reflective (e.g., have one or more reflective surfaces) such that alignment of the particles 18 in the presence of a magnetic field makes the film 10 appear brighter or darker based on the spatial orientation of the film 10 relative to the magnetic field.

During use, the film 10 is placed outside the patient (e.g., abdominal cavity "C" of FIGS. 3A-B) or over a region of tissue in which a surgical procedure is being performed. In embodiments, the film 10 may be used internally over organs and other tissue to track location of medical devices therein. Localization and/or tracking of medical devices is accomplished by monitoring changes in color (e.g., darkness level) of the film 10 as described in further detail below with respect to FIGS. 4, 6 A-B, and 7, Suitable medical devices include medical implants, such as, meshes, stents, sponges, fasteners (e.g., staplers), slings, clips, sutures, combinations thereof, and the like. In embodiments, the magnetic elements may be electromagnets. In further embodiments, the medical devices may include one or more components (e.g., housing, shaft, etc.) that are magnetized or include a coating of magnetic microparticles.

Figure 3A:
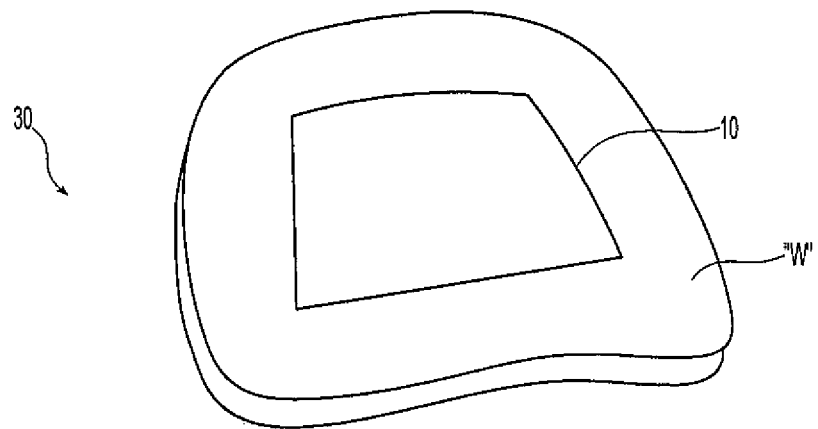
FIG. 3A is a perspective view of the magnetic field visualization film of FIG. 1 disposed over abdominal cavity according to the present disclosure.
Figure 3B:
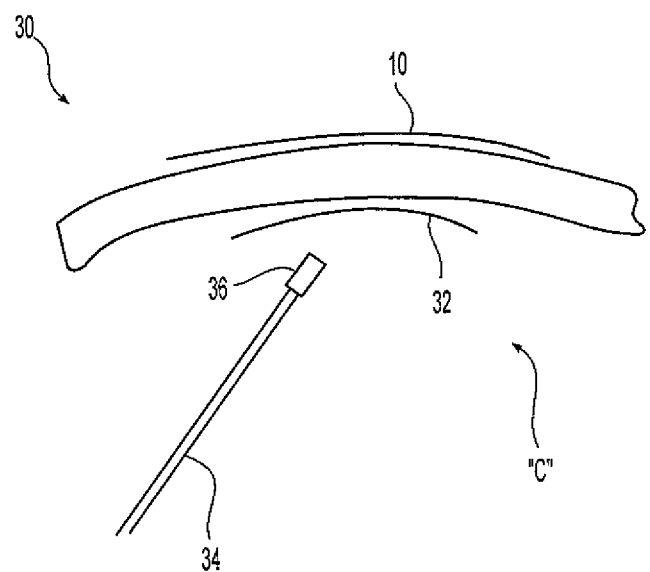
FIG. 3B is a cross-sectional view of the abdominal cavity with the magnetic field visualization film of FIG. 1 disposed outside of the cavity and a hernia mesh with a medical instrument disposed within the cavity according to the present disclosure.

FIGS. 3A-B show a system (e.g., kit) 30 for repairing a hernia according to an embodiment of the present disclosure. The system 30 includes the film 10 that is disposed over the abdominal cavity "C" (e.g., over an abdominal wall "W") and a mesh 32. Since the film 10 is formed from flexible sheets 12a, 12b, the film 10 may be conformed to the abdominal wall "W." The system 30 also includes a medical instrument 34 having one or more magnetic elements 34 disposed thereon. The instrument 34 may be any suitable open or endoscopic surgical instrument, such as, endoscopes, catheters, graspers, balloons, sealers, tissue staplers, vessel sealers, clip appliers, biopsy instruments, ablation probes, combinations thereof, and the like. The medical instrument 34 includes one or more magnetic elements 36, which may be formed from any suitable ferromagnetic or magnetizable material. The magnetic elements 36 are permanently or temporarily (e.g., via adapters) secured to the medical instrument 34.

Features relevant to targeting the procedure, tissue or the medical device may be sketched on the magnetic field viewing film using a magnetized stylus or "pen".

Suitable magnetic materials may be temporary magnetic materials or permanent magnetic materials, ceramic, crystalline, or flexible magnetic materials (e.g., a polymeric substance such as thermoplastics or rubber) combined with magnetic ferrite (e.g., heat-treated mixtures of oxides of iron and one or more other metals having complex crystals with magnetic properties). Suitable magnetic materials include, but are not limited to, ferrite, strontium ferrous oxide, neodymium (NdFeB, optionally including dysprosium), samarium, cobalt, aluminum, nickel, copper, iron, titanium, and combinations thereof. Magnetic elements 36 may have any suitable shape, such as, cylindrical, polygonal, (e.g., square or hexagonal cross-section), and the like. In embodiments, the magnetic element 36 may be an electromagnet. In further embodiments, the surgical instrument 34 may include one or more components (e.g., housing, shaft, etc.) that are magnetized or include a coating of magnetic microparticles (e.g., magnetic particles described above).

Figure 4:
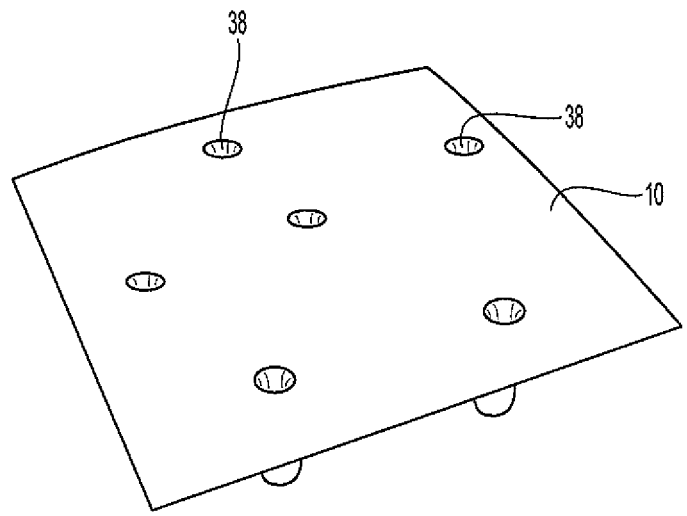
FIG. 4 is a perspective view of the magnetic field visualization film of FIG. 1 in the presence of a magnetic field produced by the medical instrument according to the present disclosure.

During use, the mesh 32 is inserted into the abdominal cavity "C" and is advanced to the site of the hernia site using any suitable methods and/or instruments. Once the mesh 32 is in position, the surgical instrument 34 is used to point to different areas of the mesh 32. With reference to FIG. 4, as the surgical instrument 34 is brought into contact with the mesh 32, the film 10 reacts to the proximity of the magnetic element 36 of the instrument 34 by changing color, which is indicative of the location of the medical devices. In particular, the magnetic particles 18 of the film 10 are free to move within the fluid 16 in response to external magnetic fields generated by the magnetic elements 36.

FIG. 4, illustrates the film 10 with multiple areas 38 indicative of the location of the magnetic element 36. When magnetic lines of force of the magnetic element 36 are parallel to the surface of the film 10, the surfaces of the magnetic particles 18 that are reflective are aligned toward the plane defined by the film 10, and appear bright. When lines of force of the magnetic field are perpendicular to the sheet, the magnetic particles 18 appear darker, since the reflective surfaces thereof are rotated away from the horizontal plane defined by the film 10. The user may keep adjusting the position of the mesh 32 and keep pointing the magnetic element 36 to various positions of the mesh 32 (e.g., corners, perimeter, center, etc.) until the mesh 32 is disposed over the desired location.

Figure 5A:
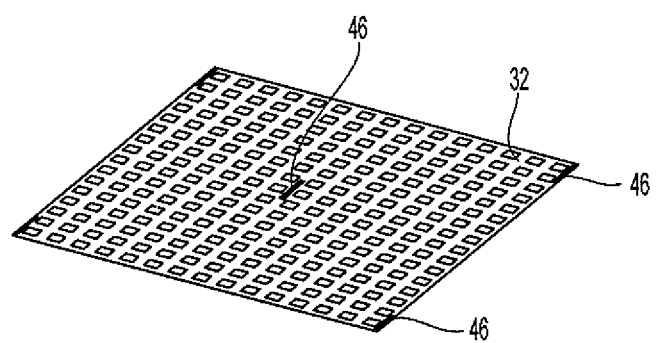
FIG. 5A is a perspective view of the hernia mesh of FIG. 3B having a plurality of magnetic elements according to the present disclosure.
Figure 5B:
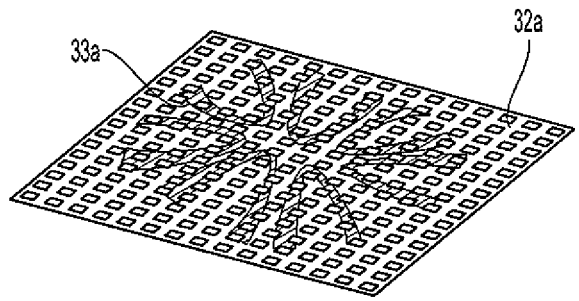
FIG. 5B is a perspective view of the hernia mesh of FIG. 3B having a magnetic pattern according to the present disclosure.
Figure 5C:
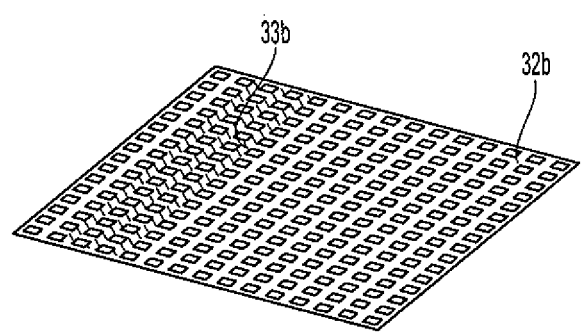
FIG. 5C is a perspective view of the hernia mesh of FIG. 3B having a linear magnetic pattern according to the present disclosure.

With reference to FIG. 5A, the mesh 32 may include one or more magnetic elements 46 disposed thereon. The magnetic elements 46 may be disposed in any suitable configuration, such as corners, center, perimeters, and combinations thereof. In further embodiments, the mesh 32 may include a plurality of magnetic microparticles disposed on and/or within the mesh 32. As shown in FIGS. 5B and 5C, the microparticles may be applied in a flower-shaped pattern 33a to a mesh 32a, a pattern 33b having a plurality of lines to a mesh 32b. The microparticles may be applied to the mesh 32 using any suitable method, such as spraying, dipping, incorporating into the polymer solution prior to forming the mesh 32, and combinations thereof. The microparticles may be applied to the mesh 32 in any suitable pattern that identifies the shape of the mesh 32.

Figure 6A:
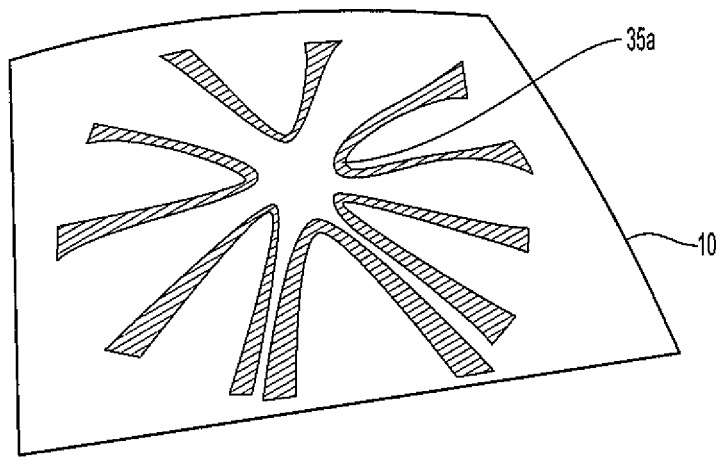
FIG. 6A is a perspective view of the magnetic field visualization film of FIG. 1 in the presence of a magnetic field produced by the hernia mesh of FIG. 5B according to the present disclosure.
Figure 6B:
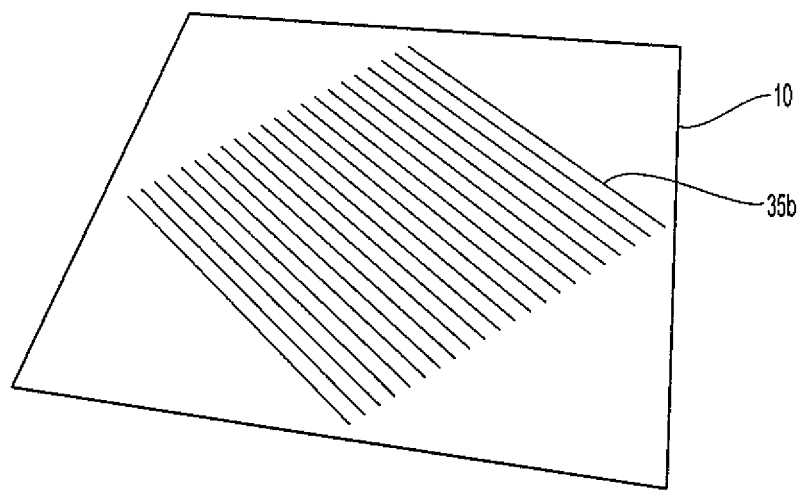
FIG. 6B is a perspective view of the magnetic field visualization film of FIG. 1 in the presence of a magnetic field produced by the hernia mesh of FIG. 5C according to the present disclosure.

With reference to FIGS. 6A and 6B, two exemplary embodiments of the patterns 33A and 33B on the film 10 are shown. FIG. 7A shows a flower-shaped pattern 35a, which is suitable for identifying the center and/or perimeter of the mesh 32a of FIG. 5B as it is brought into proximity with the film 10. FIG. 7B shows a pattern 35b having a plurality of lines corresponding to the pattern 33b of the mesh 32b, which is suitable for identifying thickness of the tissue disposed between the mesh 32 and the film 10, with the lines acting like contour lines.

Figure 7:
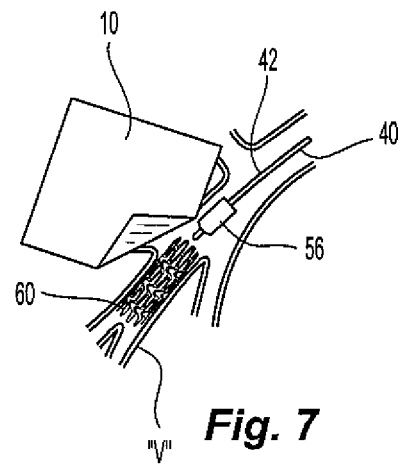
FIG. 7 is a cross-sectional view of a blood vessel with a magnetic stent and a magnetic catheter disposed therein and the magnetic field visualization film of FIG. 1 disposed over the tissue according to the present disclosure.

FIG. 7 shows another embodiment of a surgical instrument (e.g., catheter 40) inserted into a blood vessel "V." The catheter 40 may be any suitable catheter having a flexible longitudinal body 42. The catheter 40 includes one or more magnetic elements 56 disposed on the longitudinal body 42. In embodiments, the magnetic element 56 may be disposed at a distal end thereof. In use, the catheter 40 is inserted into the vessel "V" with the film 10 disposed over the treatment site. The magnetic elements 56 cause the film 10 to change in color as described above.

Figure 8:
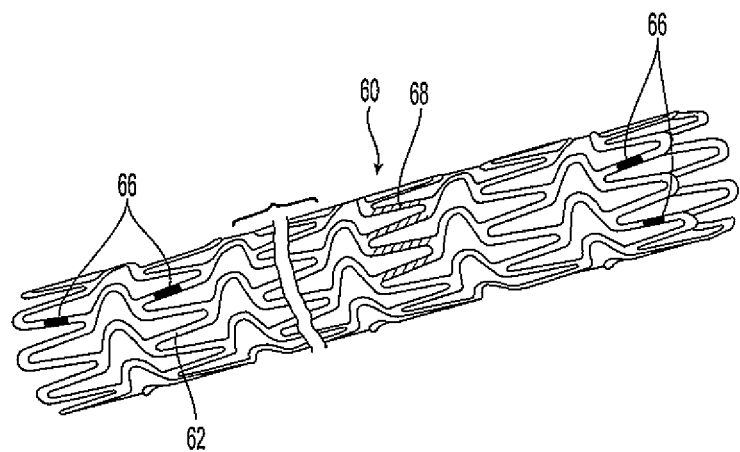
FIG. 8 is a perspective view of the magnetic stent of FIG. 8 according to the present disclosure.
Figure 9:
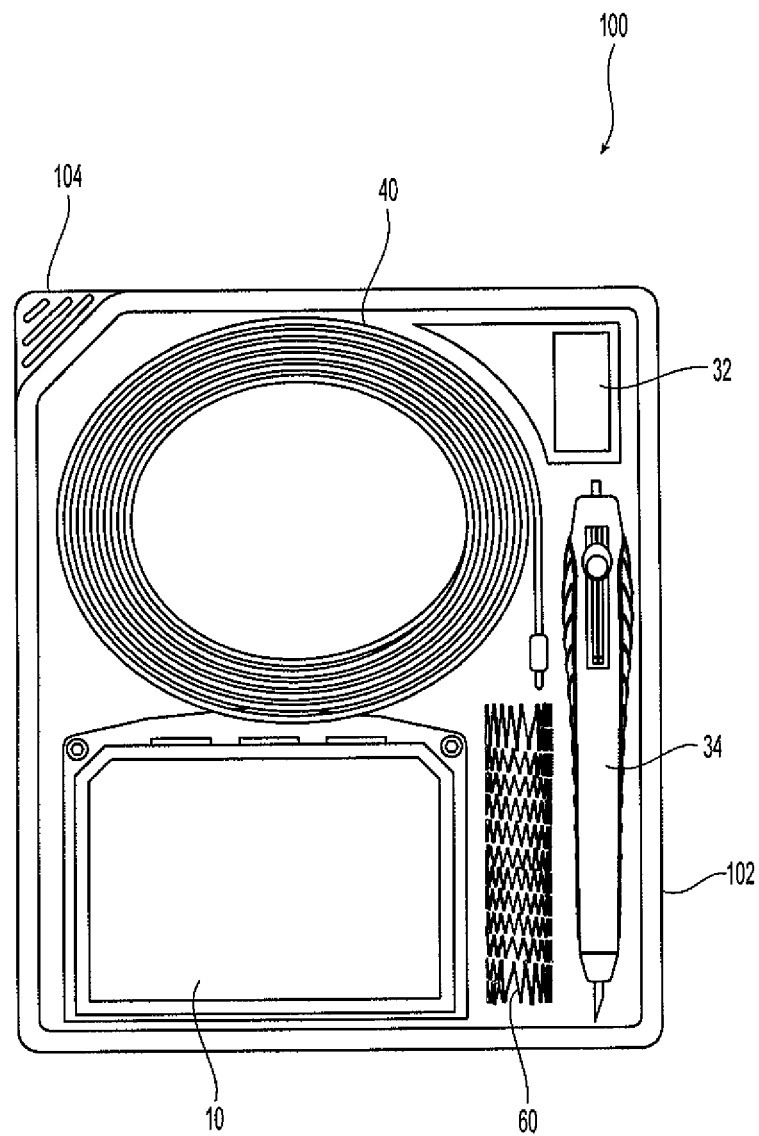
FIG. 9 is a top view of a surgical kit according to the present disclosure.

With reference to FIGS. 7 and 8, the catheter 40 may be used to deliver various medical devices into the vessel "V,"

such as a stent 60. The stent 60 includes a plurality of interconnected struts 62. The stent 60 may include one or more magnetic elements 66 disposed thereon. The magnetic elements 66 may be disposed in any suitable configuration. In further embodiments, the stent 60 may include a plurality of magnetic microparticles disposed on (e.g., applied as a pattern 68) and/or within the stent 60. The microparticles may be applied to the stent 60 using any suitable method, such as spraying, dipping, incorporating into the polymer solution prior to forming the stent 60, and combinations thereof. The microparticles may be applied to the stent 60 in any suitable pattern.

The present disclosure also provides for a surgical kit 100, having one or more magnetic field visualization films 10 and one or more of the following: the mesh 32, the surgical instrument 34, the catheter 40, and the stent 60. In embodiments, the surgical kit 100 may include any other medical instruments and/or devices having magnetic elements, magnetized components, or other means suitable for generating magnetic fields (e.g., electromagnets) that are detectable by the film 10.

The kit 100 may include a tray 102 having a plurality of planar surfaces and a plurality of recesses that may be disposed within the planar surfaces. The tray 102 may be formed of any suitable material, for example the tray 102 may be molded from a transparent or translucent substantially rigid plastic material (i.e., PETG). The tray 102 may have side walls defining a depth of the tray 102. The planar surfaces may be vertically offset within the tray 102. The tray 102 including its features (e.g., planar surfaces, recesses, walls, etc.) may be formed by molding or any other suitable techniques.

The plurality of recesses are adapted to hold articles or implements (e.g., films 10, the mesh 32, the surgical instrument 34, the catheter 40, the stent 60, etc.) that are useful in performing the intended surgical procedures described above. Each recess may be adapted to hold one or more articles (e.g., a plurality of films 10 or meshes 32 arranged in a stack). The recesses may also include detents, protrusions, or the like to frictionally engage the articles and positively retain the articles within the respective recesses.

The kit 100 may also include a cover (not shown) to enclose the articles therein. A corner 104 of the tray 102 may be configured so that the cover is not adhered to the corner 104. In such an embodiment, a user may grasp the cover that is positioned adjacent to the corner 104 to remove the cover from the tray 102. The cover may be attached or configured with the tray by any suitable method, including but not limited to adhesives, heat sealing, sonic or thermal welding, solvents, etc. After all of the articles have been placed in the tray 102 and the cover sealed to the tray, the kit is subjected to an ETO (ethylene oxide) gas sterilization process. A suitable cover material is TYVEK™ a spunbond polyolefin, from DuPont of Wilmington, Del. Any number of other permeable web materials suitable for sterilization (ETO), such as Kraft paper, may be used as the cover. The kit 100 may also include a pamphlet (not shown) that includes various information, such as directions for using the kit 100.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method comprising:
   placing a magnetic field viewing film over a region of tissue;
   placing a hernia mesh at a position at least partially within the region of tissue, the hernia mesh including a plurality of magnetic microparticles disposed in a pattern, the pattern including a plurality of contour lines suitable for determining the tissue thickness;
   determining a location of the hernia mesh based on a visualization by the magnetic field viewing film of a magnetic field produced by the plurality of magnetic microparticles; and
   determining tissue thickness based on the pattern.

2. The method according to claim 1, wherein the magnetic field viewing film comprises at least one flexible sheet and a plurality of magnetic particles responsive to the magnetic field produced by the plurality of magnetic microparticles.

3. The method according to claim 1, further comprising:
   adjusting the location of the hernia mesh based on the visualization by the magnetic field viewing film of the magnetic field produced by the plurality of magnetic microparticles.

4. The method according to claim 1, further comprising determining an orientation of the hernia mesh relative to the region of tissue based on the pattern, the pattern including a plurality of contour lines suitable for determining the orientation of the hernia mesh.

5. A method comprising:
   placing a magnetic field viewing film over a region of tissue;
   guiding a hernia mesh using a medical instrument to a position at least partially within the region of tissue, the hernia mesh including a plurality of magnetic microparticles disposed in a pattern, the pattern including a plurality of contour lines suitable for determining the tissue thickness;
   determining a location of the hernia mesh based on a visualization by the magnetic field viewing film of a magnetic field produced by the plurality of magnetic microparticles; and
   determining tissue thickness based on the pattern.

6. The method according to claim 5, further comprising:
   adjusting the location of the hernia mesh based on the visualization by the magnetic field viewing film of the magnetic field produced by the plurality of magnetic microparticles.

7. The method according to claim 5, wherein the magnetic field viewing film comprises at least one flexible sheet and a plurality of microspheres encapsulating at least one magnetic particle responsive to the magnetic field produced by the plurality of magnetic microparticles.

8. The method according to claim 5, further comprising determining an orientation of the hernia mesh relative to the region of tissue based on the pattern, the pattern including a plurality of contour lines suitable for determining the orientation of the hernia mesh.

9. A kit comprising:
   a magnetic field viewing film; and
   a hernia mesh including a plurality of magnetic microparticles producing a magnetic field capable of being visualized by the magnetic field viewing film, wherein the plurality of magnetic microparticles are arranged in a configuration suitable for determining tissue thickness.

10. The kit according to claim 9, further comprising instructions for use of the kit, the instructions comprising:

placing the magnetic field viewing film over a region of tissue;

placing the hernia mesh at a position at partially within the region of tissue; and determining a location of the hernia mesh based on a visualization by the magnetic field viewing film of the magnetic field produced by the plurality of magnetic microparticles.

11. The kit according to claim 10, the instructions further comprising:

adjusting the location of the hernia mesh based on the visualization of the magnetic field viewing film.

12. The kit according to claim 9, wherein the magnetic field viewing film comprises at least one flexible sheet and a plurality of magnetic particles responsive to the magnetic field produced by the plurality of magnetic microparticles.

13. The kit according to claim 9, wherein the plurality of magnetic microparticles are arranged in a configuration suitable for determining an orientation of the mesh relative to the region of tissue.

* * * * *